(12) United States Patent
Miller et al.

(10) Patent No.: US 6,518,064 B1
(45) Date of Patent: Feb. 11, 2003

(54) PINK BOLLWORM EXPRESSION SYSTEM FOR COMMERCIALLY VALUABLE PROTEIN PRODUCTION

(75) Inventors: Thomas A. Miller, Riverside, CA (US); John J. Peloquin, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/538,404

(22) Filed: Mar. 29, 2000

(51) Int. Cl.⁷ .......................... C12N 15/00; C12N 15/63
(52) U.S. Cl. ................... 435/325; 435/320.1; 435/69.1; 435/91.4; 435/455; 536/23.1; 536/24.1
(58) Field of Search .............................. 536/23.1, 24.1; 435/320.1, 455, 325, 69.1, 91.4

(56) References Cited

PUBLICATIONS

Ngo et al., in: The Protein Folding Problems and Tertiary Structure Prediction, 1994, Merz et al., (ed.), Birkhauser, Boston, MA, pp. 492–495.*
Mikkelsen, TIG, 1993, vol. 9, p. 159.*
Chiu et al. Folding & Design, 1998, vol. 3, No. 3, pp. 223–228.*
Handler, Alfred M., et. al., "The lepiopteran transposon vector, piggyBac, mediates germ–line transformation in the Mediterranean fruit fly" Proc. Natl. Acad. Sci. USA, 1998, 95:7520–7525.

Lobo, N., et al., "Transposition of the piggyBac element in embryos of Drosophila melanogaster, Aedes aegypti and Trichoplusia ni" Mol. Gen. Genet., 1999, 261:803–810.

Farrell, Patrick J., et al., "High–Level Expression of Secreted Glycoproteins in Transformed Lepidopteran Insect Cells Using a Novel Expression Vector" Biotechnol., Bioeng., 1998, 60:656–663.

Mange, Alain, et al., "A Strong Inhibitory Element Down-regulates SRE–stimulated Transcription of the A3 Cytoplasmic Actin Gene of Bombyx mori" J. Mol. Biol., 1997, 265:266–274.

Toshiki, Tamura, et al., "Germline transformation of the silkworm Bombyx mori L. using piggyBac transposon–derived vector" Nat. Biotechnology, 2000, 18:81–84.

* cited by examiner

*Primary Examiner*—Dave T. Nguyen
(74) *Attorney, Agent, or Firm*—Townsend and Townsend and Crew LLP

(57) ABSTRACT

The present invention is directed to a method for transforming insects, in particular Lepidoptera. The invention provides promoters and vectors, as well as methods for transforming insect cells and insects. The invention further provides a method for protein production using heterologous protein expression in insect cultured cells and in insects. The methods of the present invention are also useful for marking insects.

14 Claims, 1 Drawing Sheet

PINK BOLLWORM EXPRESSION SYSTEM FOR COMMERCIALLY VALUABLE PROTEIN PRODUCTION

BACKGROUND OF THE INVENTION

A variety of systems, both prokaryotic and eukaryotic, are available for producing therapeutically important proteins. The use of prokaryotic systems is, however, limited, since prokaryotic cells cannot carry out the post-translational modifications that are often essential for the function of eukaryotic proteins. In addition, secretion of eukaryotic proteins is often inefficient in prokaryotic systems, and folding of the produced protein is absent or incorrect. A number of eukaryotic systems have also been developed. Such eukaryotic expression systems can successfully express native and active proteins that are not capable of being produced in prokaryotic systems. Mammalian systems are however expensive and zoonoses, in particular prion diseases, may be transmitted by use of mammalian products (e.g., Fetal Calf Serum) in in vitro culture systems. Furthermore, many desirable proteins, such as anti-clotting factors or peptide hormones may have activity in mammalian or vertebrate systems that prevent their expression in these systems. For example, anti-clotting factors produced in large amounts in mammals would likely be fatal to those animals due to lack of clotting, obviating the production of these materials in a mammalian system. Insects systems offer an alternative to mammalian systems. Insect systems are cheaper and are not associated with the same health issues as their mammalian counterparts. However, to date, the available insect systems is limited and they do not allow large scale protein production without cell culture.

Many insects, and in particular Lepidopteran species, are key pests on food and fiber crops worldwide. Field resistance to pesticides presents an increasing challenge to pest control. Furthering the ability to manipulate insect species at the molecular level will become more important to advance our understanding of insect biology and to promote the development of novel field applications. As an example, germ-line transformation can directly contribute to pest control efforts, for instance, through indelible genetic marking of insects produced for Sterile Insect Technique (SIT) programs.

The utility of transposable elements to manipulate an insect genome has been shown in Drosophila with the P element (Rubin and Spradling (1983); Spradling and Rubin (1982)). However, the host range of P is restricted to closely related drosophilids (O'Brochta et al. (1991) *Mol. Gen. Genet.* 225:387–394; O'Brochta et al. (1994) *Mol. Gen. Genet.* 244:9–14)). The discovery of new elements with broader host ranges such as mariner (Coates et al. (1995) *Mol. Gen. Genet.* 249:246–252), Minos (Loukeris et al. (1995) *Science* 270:2002–2005), Hermes (O'Brochta et al. (1996) *Insect Biochem. Mol. Biol.* 26:739–753; Sarkar et al. (1997) *Genetica* 99:15–29; Sarkar et al. (1997) *Insect Biochem. Mol. Biol.* 27:359–363), and piggyBac (Loukeris et al., supra) has led to the development of vector systems for transformation of further insect species including the medfly, *Ceratitis capitata* (Loukeris et al., supra), the mosquito *Aedes aegypti* (Jasinskiene et al. (1998) *Proc. Natl. Acad. Sci. USA* 95:3743–3747; Coates et al. (1998) *Proc. Natl. Acad. Sci. USA* 95:3748–3751) and the domestic silkworm *Bombyx mori* (Toshiki et al. (2000) *Nature Biotech.* 18:81–84). Most successful germ-line transformation events have been described for Dipteran species.

There is therefore a need in the art for insect transformation and protein expression systems, for protein production and for other uses, such as insect marking for pest control studies. The present invention addresses these and other needs.

SUMMARY OF THE INVENTION

The present invention provides promoters, expression cassettes, expression vectors and host cells for expressing heterologous proteins in insects. The invention further provides a method for transforming insect cells, in particular from a Lepidopteran, and for obtaining transgenic insects. The methods of the present invention can be used for, for example, to produce a protein of interest or to mark insects using marker proteins.

In one aspect, the present invention is directed to an isolated nucleic acid molecule comprising a promoter sequence having at least 90% identity with the sequence set forth in SEQ ID NO:1. In one embodiment, the promoter has the sequence of SEQ ID NO:1. The present invention further provides an expression cassette comprising the promoter sequence operably linked to a nucleic acid sequence encoding a protein of interest. In some embodiments, the expression cassette further comprises a transcriptional enhancer. In other embodiments, the expression cassette further comprises a regulatory sequence that controls the tissue-specific expression of the protein of interest. In some embodiments, the protein is a fluorescent marker. The fluorescent marker can be, for example, the enhanced green fluorescent protein, derivatives therof or DSred. In another embodiment, the protein of interest is a therapeutic protein. In other embodiments, the nucleic acid sequence is linked to the promoter sequence in an antisense orientation.

The present invention also provides expression vectors and host cells comprising the expression cassette described above. In some embodiments, the expression vector is a transposable element, for example, piggyBac. The piggyBac transposable element of the invention preferably lacks a 1.023 kb fragment from the Open Reading Frame encoding the transposase.

In other aspects, the invention is directed to transgenic insects comprising the expression cassette described above. In some embodiments, the transgenic insect is a Lepidopteran, such as the pink bollworm. In other embodiments, the insect is a Dipteran.

The present invention further provides a method for transforming an insect cell comprising introducing into the cell an expression cassette of the invention. In some embodiments, the cell is a pre-zygotic egg cell. In some embodiments, the pre-zygotic egg cell is allowed to develop into an insect. In other embodiments, the cell is within an insect. The insect cell can be from a Lepidopteran, such as a pink bollworm. In one aspect, the insect cell is cultured to obtain a cell culture, and the protein of interest is purified from the cell culture. In another aspect, the expression cassette comprises a nucleic acid sequence encoding a marker protein.

The present invention further provides a method for producing a protein comprising introducing into an insect cell an expression cassette, allowing the cell to develop into an insect, and purifying the protein of interest from the insect or its progeny.

BRIEF DESCRIPTION OF THE DRAWINGS

FIG. 1 shows a map of the pB[BmA3EGFP] transformation vector used to express the Enhanced Green Fluorescent

Figure 1:
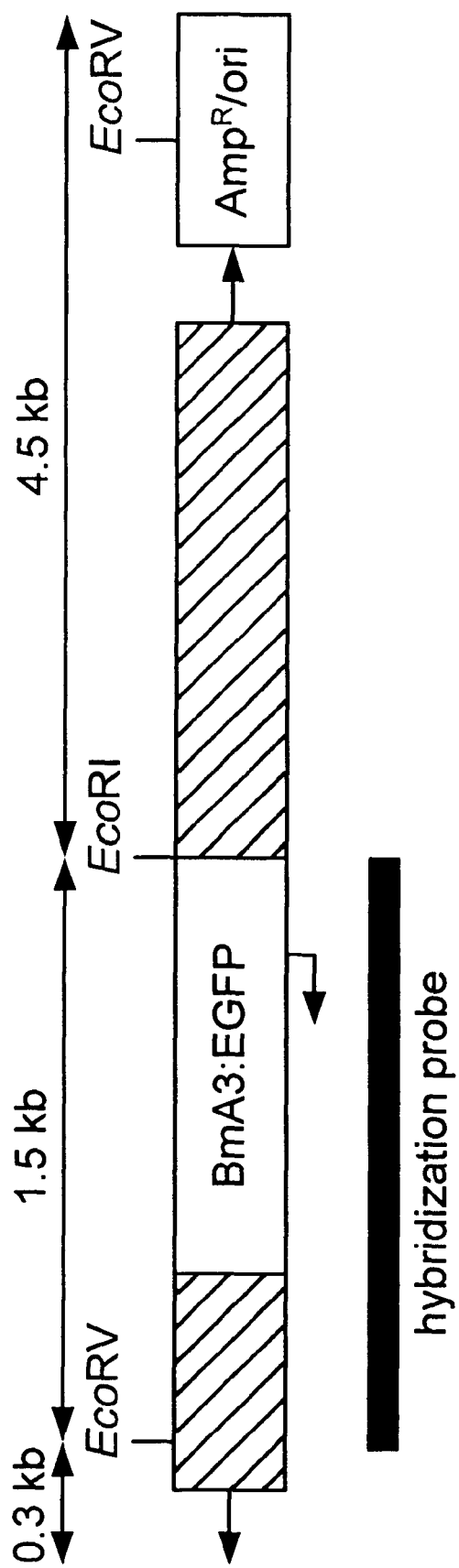

Protein (EGFP) under the control of a *Bombyx mori* actin 3 promoter in pink bollworms. "BmA3:EGFP" corresponds to the expression cassette comprising the EGFP coding sequence operably linked to the modified actin 3 promoter from *Bombyx mori*. The sequence used as a hybridization probe for analysis of the transformants is also shown.

DESCRIPTION OF THE SPECIFIC EMBODIMENTS

I. Introduction

The present invention provides novel promoters for expression of heterologous proteins in insect cells, in particular in insects of the order Lepidoptera. The present invention also provides new transposable elements useful for transforming Lepidoptera (e.g., pink bollworms) and other insects. The present invention is further directed to methods for producing proteins in insects as well as for marking insects.

In particular, the present invention provides modified promoters from the actin 3 gene of *Bombyx mori* that allow strong expression of heterologous proteins in Lepidoptera and other insects. As shown below, the transposable element piggyBac is useful for transforming Lepidoptera, such as the pink bollworm, and other insects. It has also been found that deletion of a large fragment of the Open Reading Frame encoding the piggyBac transposase does not affect the capacity of the vector to integrate into the genome of the host cell. Using the piggyBac vector, proteins can be expressed in insects under the control of the modified actin 3 promoter. This system allows the mass production of proteins in insect cell cultures or whole insects.

II. Definitions

As used herein, the following terms have the meanings ascribed to them below unless specified otherwise.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605–2608; Rossolini et al. (1994) *Mol. Cell. Probes* 8:91–98). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g. hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "conservative substitution" applies to both amino acid and nucleic acid sequences. With respect to particular nucleic acid sequences, conservative substitutions refers to changes in the nucleic acid sequence that result in nucleic acids encoding identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acid sequences, refer to two or more sequences or subsequences that are the same or have a specified percentage of nucleotides that are the same (i.e., 60%, 65%, 70%, 75%, 80%, or 85% identity, preferably 90% or 95% identity over a specified window region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Preferably, the identity exists over a region that is at least about 25 nucleotides in length, or more preferably over a region that is 50–100 nucleotides in length. For sequence comparison, typically one sequence acts as a reference sequence, to which test sequences are compared.

Optimal alignment of sequences for comparison may be conducted by the local identity algorithm of Smith and Waterman (1981) *Add. APL. Math.* 2:482, by the identity alignment algorithm of Needleman and Wunsch (1970) *J. Mol. Biol.* 48:443, by the search for similarity method of Pearson and Lipman (1988) *Proc. Natl. Acad. Sci. (USA.)* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art.

A preferred example of algorithms that are suitable for determining percent sequence identity and sequence similarity are the BLAST and BLAST 2.0 algorithms, which are described in Altschul et al. (1977) *Nuc. Acids Res.* 25:3389–3402 and Altschul et al. (1990) *J. Mol. Biol.* 215:403–410, respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/). Cumulative scores are calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

Another indication that nucleotide sequences are substantially identical is if two molecules hybridize to each other, or to a third nucleic acid, under moderately, and preferably highly, stringent conditions. Stringent conditions are sequence dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point $(T_m)$ for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 50° C., usually 60° C. and often 65° C.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression cassette" is a nucleic acid construct, generated recombinantly or synthetically, with a series of specified nucleic acid elements that permit transcription of a particular nucleic acid in a host cell. The expression cassette can be part of a plasmid, virus, nucleic acid fragment, or be integrated into the genome of a host cell. Typically, the expression cassette includes a nucleic acid to be transcribed operably linked to a promoter.

In the context of the present invention, a "marker protein" refers to any protein that can be easily detected. Preferred "marker proteins" include, for example, those that are fluorescent or calorimetric markers, as well as enzymes that have an easily detectable activity.

The term "pre-zygotic eggs," refers to eggs that have been fertilized, but in which the pronuclei have not fused yet.

III. General Recombinant Nucleic Acid Techniques

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences.

Oligonucleotides that are not commercially available can be chemically synthesized according to the solid phase phosphoramidite triester method first described by Beaucage and Caruthers (1981) *Tetrahedron Letts.* 22:1859–1862, using an automated synthesizer, as described in Van Devanter et al. (1984) *Nucleic Acids Res.* 12:6159–6168. Purification of oligonucleotides is by either native acrylamide gel electrophoresis or by anion-exchange HPLC as described in Pearson and Reanier (1983) *J. Chrom.* 255:137–149.

The sequence of the cloned genes and synthetic oligonucleotides can be verified after cloning using, e.g., the chain termination method for sequencing double-stranded templates of Wallace et al. (1981) *Gene* 16:21–26.

A. Cloning a Promoter Sequence

One of skill will recognize that promoter sequences other than the exemplified sequence can be used in the context of the present invention. Typically, the promoter sequences are those from genes that are expressed during the late stages of embryogenesis, preferably after the gastrula stage, and/or in larval and adult tissues. Preferably, the promoter sequences will be predominantly active in a subset of tissues, rather than being ubiquitous. For example, a suitable promoter may be predominantly active in tissues of endodermal origin, such as the midgut.

Here and throughout the specification, a preferred promoter is the actin 3 promoter from *Bombyx mori* as exemplified below.

In general, the nucleic acid sequences corresponding to a promoter of interest and related nucleic acid sequence homologs are cloned from genomic DNA libraries by hybridization with a probe, or isolated using amplification techniques with oligonucleotide primers. For instance, actin 3 promoter sequences are typically isolated from *Bombyx mori* genomic libraries by hybridizing with a nucleic acid probe, the sequence of which can be derived from SEQ ID NO:1.

Amplification techniques using primers can also be used to amplify and isolate a polynucleotide sequence corresponding to a promoter of interest (e.g., the actin 3 promoter) from DNA. Degenerate primers (e.g., primers derived from SEQ ID NO:1) can be used to amplify a promoter sequence (e.g., the actin 3 promoter sequence) (see, e.g., Dieffenfach and Dveksler, *PCR Primer: A Laboratory Manual* (1995)). These primers can be used, e.g., to amplify either the entire promoter sequence or a probe which is then used to screen a library (e.g., a *Bombyx mori* genomic library) for the entire promoter sequence.

1. Genomic libraries

Promoter sequence polymorphic variants, alleles, and interspecies homologs that are substantially identical to the promoter sequence of interest can be isolated using promoter sequence nucleic acid probes, and oligonucleotides under stringent hybridization conditions, by screening genomic libraries.

For constructing a genomic library, the DNA is extracted from the tissue or the whole animal (e.g., *Bombyx mori*) and is either mechanically sheared or enzymatically digested to yield fragments of about 12–20 kb. The fragments are then separated by gradient centrifugation from undesired sizes and are constructed in bacteriophage lambda vectors. These vectors and phages are packaged in vitro. Recombinant phage are analyzed by plaque hybridization as described in Benton and Davis (1977) *Science* 196:180–182. Colony hybridization is carried out as generally described in Grunstein et al. (1975) *Proc. Natl. Acad. Sci. USA*, 72:3961–3965.

2. Amplification methods

An alternative method of isolating a nucleic acid sequence corresponding to a promoter of interest and its homologs combines the use of synthetic oligonucleotide primers and amplification of DNA template (see, U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify promoter nucleic acid sequences directly from genomic libraries. Degenerate oligonucleotides can be designed to amplify promoter sequences from homolog genes or sequences showing homology to the present promoter. For example, oligonucleotides can be designed using the sequences provided herein to amplify sequences homologous to the *Bombyx mori* actin 3 promoter. Restriction endonuclease sites can be incorporated into the primers to facilitate cloning. Polymerase chain reaction or other in vitro amplification methods may also be useful, for example, for nucleic acid sequencing, or for other purposes. Sequences amplified by the PCR reaction can be purified from agarose gels and cloned into an appropriate vector.

In one embodiment, high density oligonucleotide analysis technology (e.g., GeneChip™) is used to identify homologs and polymorphic variants of the promoter sequence (e.g., the actin 3 promoter of *Bombyx mori*).

B. Modifying a Promoter Sequence

The present invention is based, at least in part, on the discovery that modifications of the promoter sequences result in significantly higher levels of expression of the heterologous sequence regulated by the promoter, and might also increase the stability of the expressed protein and/or the viability of the transfected cells and/or the transformed animals. These modifications include, for example, the deletion of repressor sequences (silencers), while activator sequences (enhancers) and other sequences essential for expression are preserved.

For example, sequences required for the initiation of RNA synthesis, e.g., the TATA box, are essential for expression and are conserved in the modified promoter. In addition, the region comprising the translation initiation ATG codon is essential for expression of the protein. The initiating ATG codon typically lies within a sequence that conforms to the consensus sequence for translation initiation as defined by Kozak ((1989) *J. Cell Biol.* 108:229–241). These "Kozak" sequences are typically preserved within the modified promoters of the present invention.

Typically, repressor sequences within the promoter sequence are removed in order to obtain higher expression levels. For example, RA3 silencer sequences (Mangé et al. (1997) *J. Mol. Biol.* 265:266–274) are deleted from the original promoter. Additional suitable modifications include, for example, removal of tissue-specific repressor sequences, conservation of enhancer sequences, such as the SRE activator element of the *Bombyx mori* actin 3 promoter (Mangé et al., supra), etc. Enhancer and silencer regions can be identified based on their nucleotide sequence (i.e., by identifying the presence of a repressor or activator consensus site) or by standard techniques in the art. For example, a variety of deletions can be made to a promoter sequence and the activity of the resulting truncated promoter can be tested following transient expression in a cell (see, e.g., Mangé et al., supra), or in vivo, for example in transformed insects. In both cases, reporter genes operably linked to the modified promoter are typically used to analyze the promoter activity.

The above-described sequence modifications may be introduced using standard recombinant techniques. For example, a particular region of the original promoter that corresponds to the sequence that needs to be conserved in the modified promoter can be amplified by methods such as polymerase chain reaction (PCR) and ligase chain reaction (LCR) using specific primers as described supra (see U.S. Pat. Nos. 4,683,195 and 4,683,202; Innis et al. (1990), supra). Restriction endonuclease sites can be incorporated into the primers to facilitate the cloning of the amplified sequences into an appropriate vector. Alternatively, if the regions of interest are not adjacent (i.e., if regions located in the middle of the promoter need to be removed), the regions that need to be preserved can be amplified separately and subsequently linked together using standard molecular biology techniques. Alternatively, appropriate restriction enzymes can be used to digest the isolated promoter sequence and the fragments corresponding to the sequences of interest can be ligated together to reconstruct a suitable modified promoter.

In addition, mutations (e.g., mutations disrupting a regulatory sequence within the promoter) can be introduced at particular loci by synthesizing oligonucleotides containing a mutant sequence, flanked by restriction sites enabling ligation to fragments of the native sequence. Following ligation, the resulting reconstructed promoter sequence encodes an analogue having the desired amino acid insertion, substitution, or deletion. Exemplary methods of making the alterations set forth above are described by Walder et al. (1986) *Gene,* 42:133; Bauer et al. (1985) *Gene,* 37:73; Craik (1985) *BioTechniques,* January: 12–19; Smith et al., *Genetic Engineering: Principles and Methods,* Plenum Press (1981); and U.S. Pat. Nos. 4,518,584 and 4,737,462.

In the context of the present invention, a preferred promoter is a promoter having a nucleic acid sequence with at least 90% identity with the sequence set forth in SEQ ID NO:1. The preferred promoter corresponds to nucleotides 1755 to 1926 of the *Bombyx mori* Actin A3 gene as described in GenBank accession U49854 (which gives the *Bombyx mori* cytoplasmic actin (A3) gene complete coding sequence).

Thus, one of skill will recognize that a number of modifications can be made to the exemplified promoter sequence without adversely affecting the function of the promoter. The activity of the modified promoter can be easily tested using standard techniques known to those of skilled in the art (e.g., transient expression in cultured cells or in vivo analysis).

D. Expression of Heterologous Sequences

The expression of natural or synthetic nucleic acids is typically achieved by constructing an expression cassette containing nucleic acid sequences encoding the protein of interest operably linked to a suitable promoter into an expression vector.

1. Constructing the expression cassette

For expression, the nucleic acid sequences that encode the protein of interest are operably linked to a promoter of the invention, using standard molecular techniques well-known to those of skill in the art. The promoter is optionally positioned about the same distance from the heterologous transcription start site as it is from the transcription start site in its natural setting. As is known in the art, however, some variation in this distance can be accommodated without loss of promoter function.

In addition to the promoter, the expression cassette, or alternatively the expression vector, contains all the additional elements required for the expression of the protein of interest in host cells. A typical expression cassette thus contains, in addition to a promoter operably linked to the nucleic acid sequence encoding the polypeptide of interest, signals required for efficient polyadenylation of the transcript, ribosome binding sites, and translation termination. The nucleic acid sequence encoding the polypeptide of interest may be linked to a cleavable signal peptide sequence to promote secretion of the encoded protein by the transfected cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites. The expression cassette should also contain a transcription termination region downstream of the structural gene to provide for efficient termination. The termination region may be obtained from the same gene as the promoter sequence or may be obtained from different genes. Alternatively, the transcription termination region can be present in the expression vector.

Epitope tags can further be added to recombinant proteins to provide convenient methods of isolation, e.g., c-myc, HA-tag, 6-His tag, or any such tag, a large number of which are well known to those of skill in the art.

2. Expression vectors

The nucleic acid encoding an expression cassette of interest is typically cloned into intermediate vectors before transformation into insect cells for replication and/or expression. Alternatively, the promoter sequence and the nucleic acid sequence encoding the protein of interest may be independently cloned into an intermediate vector for amplification. The promoter and protein-encoding nucleic acid sequences are then both cloned into the expression vector. In any case, in the expression vector, the nucleic acid sequence encoding the protein of interest is operably linked to the promoter sequence.

These intermediate cloning vectors are typically prokaryote vectors, e.g., plasmids, or shuttle vectors (i.e., vectors capable of replication in both prokaryotic and eukaryotic cells). Vectors, cells, and transfection methods are well known to those of skill and are described, e.g., in Ausubel et al. or in Sambrook et al., both supra.

Any of a variety of expression vectors known to those of ordinary skill in the art may be employed to express recombinant polypeptides of the present invention. Expression may be achieved in any appropriate host cell that has been transformed or transfected with an expression vector containing a DNA molecule that encodes a recombinant polypeptide. Suitable host cells include insect cells, for example from a Lepidopteran, a Dipteran, a Coleopteran, a Hymenopteran, etc.

A variety of vectors known to those of skill in the art can be used for transient or stable protein expression in insect cells. For a review on suitable expression systems, see, e.g., Fernandez and Hoeffler (1999) *Gene expression systems* (Acad. Press). Suitable expression vectors may remain episomal or integrate into the host cell genome. The expression vectors can have the ability to self-replicate or not, i.e., drive only transient expression in a cell. Suitable expression vectors include plasmid vectors (naked DNA) and viral vectors, in particular baculovirus vectors, which allow the integration of DNA into the host cell genome.

Typically, for protein expression, the vector system will comprise a selection marker and the insect cells will be grown under restrictive conditions, under which only the cells carrying the marker (i.e., the plasmid) can survive and/or proliferate. Such markers further result in an increase in the number of inserted plasmids. Suitable markers include, for example, neomycin, thymidine kinase, dihydrofolate reductase, hygromycin B phosphotransferase and α-amanitin.

Alternatively, high yield expression systems not involving gene amplification, such as baculovirus vectors, are also suitable. A variety of baculovirus expression vectors are publicly available, such as pAC360 (Invitrogen, San Diego, Calif.) and methods of expressing proteins using baculovirus vectors are well-known to those of skill in the art (see, e.g., U.S. Pat. Nos. 5,147,788; 5,637,477; 5,593,875; 5,762,939; and 6,033,903).

In some embodiments, naked DNA vectors are used. Such vectors offer the advantage of permitting the generation of stable cell lines. Such stable cell lines allow continuous protein production, give better reproducibility and facilitate large-scale production. When not used, stable cell lines can be frozen at −70° C.

In addition, a number of vectors can be used for transforming insect cells, (e.g., egg cells). Transformation can be carried out using vectors that are not transposable elements (see, e.g., Fox et al. (1975) *Gene Res.* 26:137–147; Germeraad (1976) *Nature* 262:229–231; Miller et al. (1987) *Science* 237:779–781; and Morris et al. (1989) *Med. Vet. Entomol.* 3:1–8). Other transformation vectors include those derived from transposable elements. Transposable elements include, but are not limited to, e.g., the P-element, the I-element, gypsy, hermes, hobo, mariner, minos, tagalong, piggyBac, etc. Some of these transposable elements (e.g., the P-element) can only transpose in certain species (e.g., drosophilids), while others have minimal restriction on host range and can be used in a variety of insect species (e.g., mariner, hermes, Minos and piggyBac). For a review on insect transformation see, for example, Ashburner et al. (1998) *Insect Mol. Biol.* 7:201–213; and O'Brochta et al. (1996) *Insect Biochem. Mol. Biol.* 26:739–753).

An expression cassette encoding the protein of interest under the control of a suitable promoter can be cloned in any of these transposable elements using standard techniques known to those of skill in the art, as described supra.

In the context of the present invention, a preferred transposable element is piggyBac (see, e.g., Thibault et al. (1999) *Insect Mol. Biol.* 8:119–23; Lobo et al. (1999) *Mol. Gen. Genet.* 261:803–810; Handler et al. (1998) *Proc. Natl. Acad. Sci. USA* 95:7520–7525; Elick et al. (1997) *Mol. Gen. Genet.* 255:605–610; Elick et al. (1996) *Genetica* 98:33–41; Fraser et al. (1996) *Insect Mol. biol.* 5:141–151; and Fraser et al. (1995) *Virology* 211:397–407). In some embodiments, piggyBac comprises an expression cassette that drives expression of a heterologous gene under the control of the modified *Bombyx mori* actin 3 promoter described supra.

Most transposable elements can be modified for use as transformation vectors, using standard molecular biology techniques. The present invention is also directed to the discovery that the entire piggyBac element is not essential for transposase-mediated transposition. The removal of a 1.023 kb fragment from the original piggyBac transposase Open Reading Frame does not affect the ability of the transposable element to transform host cells. In a preferred embodiment, the piggyBac vector of the present invention lacks approximately 1 kb from the original piggyBac transposase open reading frame.

IV. Protein Expression Systems

A. Protein Expression in Cultured Cells

Standard transfection methods are used to produce insect cell lines that express large quantities of a protein of interest, which is then purified using standard techniques (see, e.g., Colley et al. (1989) *J. Biol. Chem.* 264:17619–17622; *Guide to Protein Purification,* in *Methods in Enzymology,* vol. 182 (Deutscher, ed., 1990)). Transformation of eukaryotic and prokaryotic cells are performed according to standard techniques (see, e.g., Morrison (1977) *J. Bact.* 132:349–351; Clark-Curtiss & Curtiss, *Methods in Enzymology* 101:347–362 (Wu et al., eds, 1983).

A variety of standard insect cell lines from different insect species can be used for protein expression. Examples of such lines include, but are not limited to, *Drosophila melanogaster* lines, such as Schneider-2 (Schneider (1972) *J. Embryol. Exp Morph.* 27:353–365), Kc1 and D-Mel-2, *Spodoptera frugiperda* lines, such as Sf-9 (Zhu (1996) *J. Virol. Methods* 62:71–79) and Sf-21 (Deutschmann (1994) *Enzyme Microb. Technol.* 16:506–512), the High Five cells line derived from *Trichoplusia ni* (Parrington (1997) *Virus Genes* 14:63–72), the Ld652Y line from *Lymantria dispar* (Vaughn (1997) *In Vitro Cell. Dev. Biol. Anim.* 33:479–482), etc. In some embodiments, the cell line is a Lepidopteran cell line, such as a pink bollworm cell line.

Any of the well known procedures for introducing foreign nucleotide sequences into host cells may be used. These include the use of calcium phosphate transfection, lipofection (i.e., transfection using cationic lipids), electroporation, microinjection, viral vectors, e.g., baculovirus vectors, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell (e.g., the insect host cell) capable of expressing the protein of interest.

After the expression vector is introduced into the cells, the transfected cells are cultured under conditions favoring the expression of the protein of interest (e.g., a therapeutically valuable protein). Cells are then harvested and homogenized and the protein of interest is purified using standard techniques identified below.

B. Protein Expression in Insects

1. Transformation of insects

Typically, insects are transformed by micro-injection of DNA, although electroporation and any other suitable techniques can be used in the context of the present invention.

The transforming DNA is preferably injected into pre-blastoderm or pre-zygotic embryos in order to obtain incorporation of the transforming construct into the germ-line of the insect. Injection is preferably performed in the posterior end of the embryo. When integration into the germ-line occurs, the resulting insects are "transgenic" and can transmit the heterologous DNA to their progeny. In a preferred embodiment, the DNA is injected into "pre-zygotic eggs."

A variety of insects can be transformed, including, Diptera, such as, e.g., the fruitfly (*Drosophila melanogaster*), other Drosophilids (e.g., *Drosophila virilis, Drosophila hydei*, etc.), the medfly (*Ceratitis capitata*), the house fly (*Musca domestica*), and the mosquito *Aedes aegypti,* Coleoptera, Hymenoptera, and Lepidoptera such as, e.g., the cabbage looper moth, (*Trichoplusia ni*), the domestic silkworm (*Bombyx mori*), the codling moth (*Cydia pomonella*), the oriental fruit moth (*Grapholitha molesta*), the tomato pinworm (*Keifera lycopersicella*), the grape berry moth (*Endopiza viteana*), the artichoke plum moth (*Platyptilia carduidactyla*), the beet armyworm (*Spodoptera exigua*), the rice stem borer (*Chilo supressalis*), the Mexican rice borer (*Eoreuma loftini*), the leafroller moth (*Plantoitrix excessana*), the Asian cornborer (*Ostrinia furnacalis*), the potato tuberworm moth (*Phthorimaea operculella*), the potato tuber moth (*Scrobipalpopsis solanivora*), the tobacco stem borer moth (*Scrobipalpa heliopa*), the sugar beet moth (*Scrobipalpa ocellatella*), the tomato moth (*Scrobipalpuloides absoluta*), and the pink bollworm, *Pectinophora gossypiella*. In preferred embodiments, the transformed insect is a Lepidopteran. In a preferred embodiment, the transformed insect is the pink bollworm.

Microinjection techniques are standard and well-known to those of skill in the art (see, e.g., Rubin and Spradling (1982) *Science* 218:348–353; Kanda and Tamura (1991) *Bulliten of the National Institute of Sericultural and Entomological Science* 2:32–46; and Peloquin et al. (1997) *Biotechniques* 22:496–499). Briefly, embryos are collected and fixed on a support, such as a slide, using, e.g., glue, gelatin, double-face tape, etc. Embryos are desiccated for an appropriate amount of time (e.g., from 10 seconds to 30 minutes, preferably from 1 minute to 15 minutes) prior to injection.

Typically, the transposable vector carrying the expression cassette does not encode the transposase, which is the enzyme that allows the integration of the transposable vector into the host insect genome. The transposable vector is co-injected with a helper plasmid that encodes the transposase. This allows integration of the transposable element into the host's genome and ensures its stability once integrated. The endogenous transposase from the transposable element is preferably used for transformation. Different promoters can be used to drive expression of the transposase in the helper vector. These promoters can be endogenous or heterologous, and can be derived from the same or from a different insect species. The strength of a promoter in a given insect is not necessarily predictive of its activity in another insect (see, e.g., Coates et al. (1996) *Gene* 175:199–201).

In the context of the present invention, a preferred helper plasmid is the pBacHsp, which contains a piggybac transposase gene driven by the *Drosophila melanogaster* hsp70 heat shock promoter instead of the endogenous piggyBac promoter (Handler and Harrell (1999) *Insect Mol. Biol.* 8:449–457).

Following micro-injection, the embryos are allowed to develop under conditions suitable for the insect of interest. The transformed insects can then be analyzed using standard molecular techniques, such as, e.g., Southern Blot or inverse PCR (see, Sambrook et al.; and Ausubel et al., both supra), by in situ hybridization, or using microscopy, if the transposable vector encodes a fluorescent marker. In addition, transposition events (integration of the transposable element into the host's genome) can also be analyzed using standard genetic methods (see, e.g., Atkinson et al. (1993) *Proc. Natl. Acad. Sci. USA* 90:9693–9697; O'Brochta et al. (1994) *Mol. Gen. Genet.* 244:9–14; Sarkar et al. (1997) *Genetica* 99:15–29; Sarkar et al. (1997) *Insect Biochem. Mol. Biol.* 27:359–363).

2. Rearing of the transformed insects

Following transformation, the insects expressing the heterologous protein (or RNA) of interest are reared. Standard rearing conditions are established for many insects and are known to those of skill in the art. The present invention is also directed to the development of appropriate conditions for rearing Lepidopteran species, and in particular pink bollworms.

Many Lepidopteran species (including the pink bollworm) require a hot humid environment for successful development and low population densities or isolation of individual larvae to avoid cannibalism. High temperature and humidity can result in fungal contamination and viral infection. In addition, long term exposure of workers to adult scales can cause allergic reactions. The present invention is directed to a mass rearing facility comprising sterile diet, clean rooms, and filtered air handling systems, to mitigate the above-cited problems. Individuals are preferably reared in isolated micro-centrifuge tubes. Similarly, individual larvae are preferably reared in individual microfuge tubes, which allow easy handling of large numbers of animals with minimal disturbance to the insects. While mold contamination of diet or mite contamination are not completely eliminated, this system allows the occasional contamination to be confined to single tubes.

Pink bollworms can be reared relatively inexpensively and by the millions of individuals (and hundreds of kilograms) daily in a dedicated factory facility. This expression system is commercially competitive with any other method for production of moderate to high value proteins. Furthermore, the mass rearing factory facility for pink bollworms and thus the protein production are essentially infinitely scalable with economies of scale.

In preferred embodiments, the transformed insects are reared en masse, in the millions per day at a commercial factory, for production of heterologous proteins. The larvae or pupae form of the transformed insects can be collected, surface sterilized and homogenized aseptically. The desired heterologous protein can be extracted from the homogenate by an appropriate (and possibly protein-specific) biochemical purification process, as described infra. This system provides the advantage of not being terminal cultures. A seed culture of insects can be maintained and the progeny that are not needed for maintenance of the strain can be directed to protein production.

This protein production system offers additional advantages, such as the fact that a whole organism, with multiple organs and cell types, allows the engineering of whole biochemical pathways not available in single cell culture systems. Additionally, the wide variety of tissue types available in the pink bollworm allow for the possibility of specialized processing to take place within the organism.

In the context of the present invention, protein production is preferably carried out in pink bollworms.

IV. Purification of the Proteins of Interest

The recombinant protein of interest (e.g., a therapeutically valuable protein) can be purified from any of the suitable expression systems described above.

A recombinant protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al.; and Sambrook et al., both supra).

A number of procedures can be employed when a recombinant protein is being purified. For example, proteins having established molecular adhesion properties can be reversibly fused to the protein of interest. With the appropriate ligand, the protein of interest can be selectively adsorbed to a purification column and then freed from the column in a relatively pure form. The fused protein is then removed by enzymatic activity. Finally the protein of interest can be purified using immunoaffinity columns.

1. Solubility fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of the protein of interest can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The protein of interest can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

4. Affinity-based Techniques

Any of a number of affinity based techniques can be used to isolate a protein of interest from cells, cell extracts, or other sources. For example, affinity columns can be made using antibodies directed to the protein of interest, or physically-interacting proteins can be identified by co-immunoprecipitation or other methods. Such methods are well known to those of skill in the art and are taught, e.g., in Ausubel et al., Sambrook et al., Harlow and Lane, all supra.

V. Expression of Proteins as Markers

The methods of the present invention can also be used to introduce into an insect a nucleic acid encoding a marker. Such marking of insects can be useful for the study of insect biology, e.g., by allowing the analysis of the distribution or the behavior of the transgenic animals upon their release in a natural environment. Many efforts are also directed to the control of propagation of a number of pest insects, especially as field resistance to pesticides presents an increasing challenge to pest control. The sterile release strategy is currently undertaken in regions having growing pest populations. Lepidopteran species are key pests on food and fiber crops worldwide. In particular, the pink bollworm is a worldwide pest of cultivated cotton. The indelible genetic marking of insects produced for Sterile Insect Technique (SIT) programs can be an essential tool for improving the sterile insect technique.

In this context, the insect of interest is transformed with a vector containing a nucleic acid sequence encoding a marker protein. The marker protein can be an enzyme having an easily detectable activity (e.g., alcohol dehydrogenase, chloramphenicol acetyl transferase, alkaline phosphatase, etc.) or, preferably, a fluorescent marker (e.g., Green Fluorescent Protein (GFP), Enhanced Green Fluorescent Protein (EGFP), as well as cyan (ECFP), blue (EBFP) or yellow (EYFP) variants, or DsRed (Clontech)). Fluorescent markers offer the advantage of functioning as dominant, non-destructive markers in a variety of insects (Brand (1995) *Trends Genet.* 11:324–325).

In preferred embodiments, the pink bollworm is marked by a fluorescent marker, preferably EGFP or DsRed.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Example 1

Construction of the Transformation Vector

A complete piggyBac element was isolated from p3E1.2 as an XbaI/HindIII fragment and cloned into pGEM-7 (Promega) at XbaI/HindIII to create pGEM-7[piggyBac]. The *Bombyx mori* A3 promoter was amplified by PCR from genomic DNA using the following primers:

BMUP: 5' CCGAATTCTGATAGCGTGCGCGTTACC 3' (SEQ ID NO:2); and

BMDN: 5' CCGGATCCGAATGCGCACTGTTCGAG 3' (SEQ ID NO:3).

The BMUP primer was designed to anneal immediately 3' of the RA3 silencer region in the A3 promoter because RA3 is known to repress transcription levels (Mangé et al., supra). The promoter was then cut with EcoRI and Bam1 and cloned into pEGFP-1 (Clontech) cut with EcoRI and BamH1. The BmA3::EGFP minigene was amplified by PCR using the primers:
EGUP: 5' GGGCTGCAGGAATTCTGGAGTCGAC 3' (SEQ ID NO:4); and
EGDN: 5' GGGAAGATCTTGATGAGTTTGGACAAAC 3' (SEQ ID NO:5).

The PCR product was isolated by digestion with PstI and BglII, and cloned into pGEM-7[piggyBac] at PstI/BglII to create pB[BmA3EGFP]. This construct resulted in the removal of 1,023 bp of piggyBac ORF sequence and the insertion of the BmA3::EGFP minigene such that transcription is directed in an opposite orientation with respect to piggyBac.

Example 2

Transformation of Pink Bollworms

1. Microinjection

Pink bollworm pupae (C strain) were received weekly from the USDA/APHIS Pink bollworm Rearing Facility (Phoenix, Ariz.). Upon eclosion, adults were housed at 28° C. Adult females were allowed to oviposit onto glass slides and injections were performed according to techniques known to those of skill in the art (see, Peloquin et al., supra). A mixture of vector and helper plasmids in a buffer containing 5 mM KCl and 0.1 mM sodium phosphate at pH 6.8 was injected at different concentrations into the posterior pole. The piggyBac helper plasmid pBacHsp (Handler and Harrell, supra) was used to provide a source of transposase in trans. Although the helper plasmid utilizes a heat shock promoter to drive expression of the transposase, injected embryos were not subjected to heat shock. After injection, $G_0$ embryos were retained on glass slides and allowed to develop at 28° C. and 70% RH. Just prior to eclosion from the eggshell, single pharate larvae were transferred to a 1.5 ml Eppendorf tube (cat. 22 36 411-1) containing approximately 200 mg of pink bollworm diet (USDA/APHIS). $G_0$ larvae were allowed to develop at 28° C., 70–80% RH on a 14:10 light:dark cycle. When developing larvae reached the second instar, a 28 gauge needle was used to pierce the lid of the Eppendorf tube to permit increased gas exchange.

Injection with vector and helper plasmid concentrations at or below 500/300 µg/ml vector/helper did not result in a significant mortality among $G_0$ embryos, as shown in Table 1.

TABLE 1

Injection and transformation with varied DNA concentrations

| vector/helper (µg/ml) | injected | developed | fertile adults | EGFP + $G_1$s | transformation frequency |
|---|---|---|---|---|---|
| 500/300 | 5974 | 2183 | 86 | 3 | 3.5% |
| 800/600 | 1911 | 286 | 0 | 0 | 0 |

"Injected" refers to the number of embryos that were successfully injected with DNA. An injection was considered successful if the embryo was not disrupted or damaged to the extent that it would have little chance for further development. Embryos sustaining damage (exploded, torn, etc.) were completely destroyed and not included in subsequent data analysis. "Developed" refers to the number of injected embryos that developed to the head capsule stage, at which point they were transferred to diet in microcentrifuge tubes. Survival of injected embryos decreased at plasmid concentrations greater than 500/300 µg/ml donor/helper. DNA concentrations above 800 µg/ml were too viscous to be injected and resulted in clogged needles and destroyed embryos. DNA concentrations below 500/300 µg/ml were more easily injected, needles clogged much less frequently, if ever, and the injections were considerably less traumatic to the embryos as measured by percent survival.

2. Rearing of the transformants $G_0$ pupae were separated by sex. $G_0$ adults surviving from injected embryos in the initial series of injections were individually backcrossed to the wild type parental strain in the early generations. Of these $G_0$ adults 86 were fertile. The infertile pairings were ignored. $G_1$ progeny from $G_0$ backcrosses were examined under a fluorescent stereomicroscope during larval stages for expression of EGFP.

Adult moths were housed in separate incubators in a room dedicated for egg collection. Long term exposure of workers to adult scales can cause allergic reactions. Scales were thus vacuumed weekly and workers entering the room wore dust masks and protective outer clothing. Mating cages were constructed from 300 ml polystyrene cylinders with polypropylene snap caps in which a small hole had been cut out and covered with 500 mesh stainless steel screening. $G_0$ males were provided with 3 virgin females and $G_0$ females were provided with two males. Adults were fed a 6% sucrose solution provided via a cotton wick in each mating cage. $G_1$ eggs were collected every three days on a double layer of Masslinn®, nonwoven towel (Chicoppe Co., New Brunswick, N.J.) or later, folded white paper towel affixed to the interior lid of each mating cage. $G_1$ eggs from a single cross were transferred to a 50 ml polypropylene screw top tube along with 10–20 g of pink bollworm diet. $G_1$s were allowed to develop to first larval instar under the same conditions as $G_0$s.

Example 3

Analysis of EGFP Expression in Transformants

1. Visual analysis of EGFP expression in transformants

Transgenic $G_1$ animals expressing EGFP were easily detected during larval stages upon examination under a fluorescent stereomicroscope. Expression of EGFP driven by the BmA3 promoter was never seen in the embryo until the development of a pharate first instar larva. In these, EGFP fluorescence was observed in the gut. The intensity of EGFP fluorescence varied from line to line. From our initial injection series, expression in the gut was highest in two lines, lines 25 and 35. Line 35 also expressed EGFP to a considerable extent in fat body. Visualization of EGFP among internal tissues was not enhanced by dissection of the gut, fat body, Malpighian tubules, and other organs. Low-power examination of dissected organs of pupae and adults did not discern any EGFP expression in these stages.

In the first larval instar, EGFP expression in line 25 was seen throughout the midgut, but appeared stronger at the anterior and posterior limits of the midgut with fainter expression in between them. Thus, early instar larvae appeared nearly transparent with two bright green stripes delineating the larval midgut. As these larvae aged, expression throughout the midgut became more intense and the anterior and posterior stripe boundaries thus became less obvious in comparison.

Transgene expression in line 35 was also primarily confined to the larval midgut in early larvae. Under high magnification, patches of EGFP expression were seen in the posterior segments, fat body, and some of the epidermal and tracheole-associated cells. EGFP expression in line 35 showed more variation from individual to individual than was seen in line 25 and in another line, line 50. Fluorescent larvae ranged from those with very bright green sections throughout the body to larvae that were only faintly fluorescent with the exception of the midgut and a band in the ninth abdominal segment that could be seen with 10× magnification and was clearly visible under higher magnification.

2. Immunoblot analysis

The degree of autofluorescence in insect tissues varies among species and can present a confounding problem when scoring for EGFP by eye. In the Pink bollworm, the yolk of embryos and the fat body of larvae autofluoresce under EGFP excitatory illumination, but autofluorescence can be distinguished from EGFP as it is distinctly more yellow than green and usually much fainter. Still, in weakly expressing lines, scoring individuals as definitively positive can be difficult. A GFP-specific antibody was used to confirm expression of EGFP from the piggyBac transgene.

Total protein was extracted from EGFP positive and wild type PBW larvae by homogenization in 1.5 ml microcentrifuge tubes with Pellet Pestles® in 100 µl RIPA buffer (50 mM Tris pH 7.4, 150 mM NaCl, 1% Triton X-100, 1% Sodium Deoxycholate, 1% SDS, 5 mM PMSF; Ausubel et al., supra). Homogenates were centrifuged at 11,000×g for 1 minute. The supernatant containing soluble protein was reserved and the precipitated pellet discarded. 7.5 µl of protein extract were loaded with an equal volume of 2×SDS loading buffer (50 mM Tris HCl pH 6.8, 100 mM DTT, 2% SDS, 0.1% Bromophenol Blue, 10% glycerol) into wells of a 15% polyacrylamide Tris-SDS gel. Proteins were separated by electrophoresis for 75 minutes at 60 mA. Proteins were transferred to an Immobilon P® membrane (Millipore®, Bedford Mass., USA) using a Hoefer® (San Francisco, Calif.) TE70 semi-dry transfer apparatus at 7 V for 2 hours. The membrane was dried overnight at 4° C. and then blocked with 5% dry-milk Blotto (Sambrook et al., supra). After blocking, the primary antibody (4 ml) 1:2000 affinity-purified rabbit anti-EGFP primary antibody (Clontech, Palo Alto, Calif.) was applied to the membrane and allowed to incubate for 2 hours at room temperature. The membrane was then washed in TBST (100 mM TrisCl, pH 7.5, 150 mM NaCl, 0.1% Tween 20 ) 3 times at 10 minute intervals on a rocker. After washing, the membrane was incubated in the 1:5000 secondary, affinity-purified goat anti-rabbit secondary antibody conjugated with Horse Radish Peroxidase (Bio-Rad®, Hercules, Calif., USA) for 2 hours on a rocker at room temperature. The membrane was washed again 3 times in TBST at 10 minute intervals. After the final wash, the membrane was incubated according to the manufacturer's instructions in Amersham/Pharrnacia (Arlington Heights, Ill.) ECL® chemoluminescent reagents for 1 minute and immediately exposed to film.

Immunoblotting of soluble protein extracted from an individual of line 35 demonstrated specific binding of the primary antibody to a single band of protein. This band co-migrated with recombinant EGFP. Proteins extracted from wild type animals were not similarly recognized. A rough estimate of the amount of EGFP produced per animal can be obtained by comparing the signal strength obtained from the recombinant EGFP loaded on the gel (2.5 and 5.0 µg) with that obtained from extracts of the EGFP larva. The EGFP signal from the larva was estimated to be about 10% (250 ng) of the signal obtained from 2.5 µg of recombinant EGFP. Since the signal on the blot represents only 7.5% of the total EGFP in the larva, about 3.3 micrograms of EGFP protein were estimated to be produced per animal.

Example 4

Genetic Analysis

EGFP-positive lines were maintained as heterozygotes at the insertion locus by serial backcrosses to the wild-type strain. At the time of the backcross analysis, both lines 25 and 35 (see Example 3) had been backcrossed for four generations which would likely separate any transformed loci that were not tightly linked. Thus, the EGFP positive parental animals used in the diagnostic backcrosses were expected to be heterozygous for a single copy of the transgene. Line 25 G4 heterozygous EGFP-positive adults backcrossed to the wild type parental strain resulted in 398 progeny of which 191 EGFP positive and 207 were negative. A backcross of line 35 EGFP+G5's to wild type resulted in 555 EGFP positive and 616 negative offspring. If each allele segregated as a single dominant locus, then the expected phenotypic ratio of such a backcross is 1:1. Chi-square analysis (df=1) for line 25 ($P<0.05$) and line 35 ($P<0.01$) supports the conclusion that EGFP was transmitted as a single locus dominant gene in these families.

Example 5

Analysis of PiggyBac Insertion

1. Southern hybridization analysis

Insertion of the piggyBac element into genomic DNA was detected by Southern analysis for line 35.

For Southern analysis, genomic DNA was isolated from PBW larvae selected on the basis of their phenotype, EGFP positive or wild type, according to methods described in Example 2.

The selected larvae were placed singly in 1.5 ml microcentrifuge tubes and ground with Pellet Pestles (Kontes Glass Co. New Brunswick N.J.). Tubes were transferred to wet ice and 300 µl of lysis buffer (10 mM EDTA, 200 mM NaCl, 10 mM Tris HCl pH 8.0, 0.5% SDS, 0.06% Anti-Foam B (Sigma, St. Louis, Mo.), and 10 mg/ml RNAse A) was added. Tubes were incubated for 30 minutes at 37° C. then 10 µg/ml Proteinase K was added to each tube, mixed, and incubated 2–6 hours at 55° C. This incubation was followed by a phenol/chloroform extraction, a chloroform extraction, and removal of residual protein by 2.5 M ammonium acetate precipitation. The supernatant was transferred to a fresh tube, DNA was ethanol precipitated, washed twice in 70% ethanol, and resuspended in TE (10 mM Tris HCl, 1 mM EDTA, pH 8.0). DNA concentrations were determined by spectrophotometry or by comparison of fluorescence with known concentrations of DNA on ethidium bromide/agarose gels (Sambrook et al., supra).

Genomic DNA from a single animal was restricted, according to conditions suggested by the manufacturer, with 10 units of EcoRI restriction enzyme, 10 µg of RNAse A, and 2 mM of spermidine for two hours. 10 additional units of enzyme were added to each digest and the reactions were continued overnight. Digested DNA was ethanol precipitated and resuspended in 20 µl TE with 2 µl 10× Ficoll loading buffer (20% Ficoll 400, 0.1 M Na$_2$EDTA, pH 8, 1.0% SDS, 0.25% Bromophenol blue, 0.25% Xylene Cyanol; Ausubel et al., supra). DNA was separated by electrophoresis in a 0.8% agarose gel. Separated fragments were transferred to Gene Screen Plus® (NEN, Boston Mass.) membrane as suggested by the manufacturer's protocol for alkaline transfer.

A 1.5 kb EcoRV-EcoRI probe containing the BmA3:EGFP minigene was prepared from the vector pB[BmA3EGFP]. The hybridization probe was radiolabeled by random priming (Prime-it RmT®, Stratagene, La Jolla, Calif.). Hybridizations were performed according to the manufacturer's conditions for Gene Screen Plus® in aqueous hybridization buffer (Church and Gilbert (1984) *Proc. Natl. Acad. Sci. USA* 81:1991–1995) with the exception that after hybridization the filter was washed twice at room temperature in 2×SSC (0.3 M NaCl, 0.03 M Na$_3$citrate.2H$_2$O, pH 7.0) for 5 minutes, twice at 65° C. in 2×SSC, 1% SDS for 15 minutes, and twice in 0.1×SSC at room temperature. The damp membrane was sealed in a plastic bag and exposed to film with two intensification screens for 7 days.

Only one EcoRI site is present in the entire 6.4 kb vector-transposon construct. The linearized construct was detected as a faint signal in lanes that contained only digested plasmid DNA. If the transposon is inserted into genomic DNA, the probe should anneal to a band of at least 1.8 kb in size depending on the distance to the most proximal EcoRI site in the genome (FIG. 1). At least two insertions were detected in this line. EGFP positive individuals carried either one of the inserts or both. The probe recognized an approximately 1.9 kb band and a 2.3 kb band. As expected, the probe failed to hybridize with DNA extracted from wild-type EGFP-negative insects.

2. Inverse PCR analysis

Upon insertion at the tetranucleotide TTAA, piggyBac causes a target site duplication (Wang and Fraser (1993) *Insect Mol. Biol.* 1:109–116). Flanking sequences of piggyBac insertions were obtained by inverse PCR (Ochman et al. (1993) *Methods in Enzymology* 218: 309–321) using a modified protocol (Spradling et al. (1999) *Genetics* 153:135–177). Genomic DNA was isolated as described above from individual EGFP larvae obtained after 4 or 5 serial backcrosses to the wild type parental animals and one or two introgressive crosses leading to a single introgressed strain. The 5' flanking sequence was determined by digestion with Sau3A1 and PCR amplification with the following primers:

2781F: 5' GCGATGACGAGCTTGTTGGTG 3' (SEQ ID NO:6); and

2519R: 5' TCCAAGCGGCGACTGAGATG 3' (SEQ ID NO:7).

The flanking sequence at the 3' end was determined by digestion with HinP1 and amplification with the following primers:

4788F: 5' CCTCGATATACAGACCGATAAAAC 3' (SEQ ID NO:8); and

4447R: 5' TGCATTTGCCTTTCGCCTTAT 3' (SEQ ID NO:9).

PCR products were sequenced using the following primers:

5SEQ: 5' CGCGCTATTTAGAAAGAGAGAG 3' (SEQ ID NO:10) for 5' junctions; and

3SEQ: 5' CGATAAAACACATGCGTCAATT 3' (SEQ ID NO:11) for 3' junctions.

PCR performed on DNA isolated from wild type PBW was used to amplify a DNA fragment from the flanking DNA without the inserted transposon.

The PCR protocol was used to amplify DNA across the piggyBac insertion site in family 35.

As an internal control, a PCR reaction which would not amplify DNA including the TTAA piggyBac integration site was carried out. Two sets of primers were used. Primers #1 and #2:

1: 5' GTC ACA ACA ACA TCA AGC TG 3' (SEQ ID NO:12); and

2: 5' CTG GCT GCA TAA GCA GTT G 3' (SEQ ID NO:13)

were designed to amplify a 294 bp fragment located 3' of the TTAA piggyBac insertion site. The following two primers:

3: 5' CTT CGA TTA TTT GTA GCT CTG 3' (SEQ ID NO:14); and

2: 5' CTG GCT GCA TAA GCA GTT G 3' (SEQ ID NO:13)

(which flank the TTAA insertion site) were predicted to amplify a 377 bp fragment including the TTAA piggyBac integration site, if the 5' and 3' inverse PCR flanks were contiguous in the wild-type PBW genome. The same downstream primer, primer #2, was used in both PCR reactions. PCR conditions were 95° C. melting, 57° C. annealing, 72° C. extension for 30 seconds, for 30 cycles.

The 5' and 3' genomic sequence flanking an inserted piggyBac element from pB[BmA3EGFP] were obtained for line 35, using the inverse PCR methods described supra. Insertion at and duplication of a TTAA site were observed. No plasmid sequence outside of the transposon ends was detected. The insertion into genomic DNA occurred in a piggyBac transposase-dependent manner (Fraser et al. (1999), Fraser et al. (1995); Thibault et al.; Lobo et al.; Handler et al.; Elick et al. (1997); and Elick et al. (1996), all supra). The flanking sequence was subjected to BLAST analysis (Altschul et al. (1990) *J. Mol. Biol.* 215:403–410) against the nucleotide sequence data present in GenBank. No strong homologies to known sequences were found.

If the flanking DNA sequences amplified by inverse PCR were from both sides of the same element, then PCR DNA amplification across the wild-type insertion site with primers #3 and #2 specific to those flanking regions should amplify a DNA fragment of 377 bp. Primers #1 and #2 would not amplify across the wild type TTAA junction site and should amplify a 294 bp DNA fragment. The DNA fragment amplified by PCR from wild type DNA using these primers corresponded to the expected 377 bp size for amplified DNA flanking a single element.

Example 6

Mating and Selection Strategy

G$_1$ larvae were examined for EGFP expression under a Leica® fluorescent stereomicroscope. The larvae believed to be EGFP-positive were transferred individually to 1.5 ml Eppendorf tubes and reared to the pupal stage as described above. Pupae from EGFP positive larvae were sexed. Male pupae and female pupae were transferred to separate cages. An appropriate number of wild-type pupae of the opposite sex were added, along with 6% sucrose to each cage. The cage was closed and returned to the incubator. Ten days after emergence, an oviposition surface was placed on the cage and eggs collected. The oviposited eggs were transferred to polypropylene Fisher® 50 ml centrifuge tubes with diet. Larvae were screened for EGFP expression and the EGFP positive larvae were selected and backcrossed to the parental wild type insects as above. Five generations of backcrosses of line 35 EGFP positive adults to the wild type parental strain were performed in which adults from the EGFP larvae were always out-crossed to wild type insects until the introgressive crosses were begun. Subsequently, lines of EGFP positives were maintained by introgression of EGFP-positive insects and selection of EGFP positive progeny to eliminate wild type alleles and to build a homozygous line. Some transgenic lines have been maintained stably over 14 generations to date.

Two lines were terminated because they did not strongly express EGFP throughout the larval stage (line 25) or proved difficult for non-expert observers to reliably distinguish from the wild type insects (line 50). A transfer permit was obtained from USDA/APHIS and line 35 was transferred to the PBW rearing facility at Phoenix Ariz. The stability of the transgene is presently being evaluated under mass-rearing conditions. Favorable maintenance of this strain over several generations may lead to its eventual use as a genetically marked strain in the ongoing USDA/ARS pink bollworm SIT program.

The heterozygous EGFP-positive insects descended from the single EGFP-positive $G_1$ founder insect of Line 35 were backcrossed to the parental wild type line and the EGFP positive progeny were selected for subsequent backcrosses for 5 generations. EGFP positive insects derived from the single EGFP-positive $G_1$ founder of family 35 were selected, then "mass mated" in sibling crosses. After two generations of introgression, EGFP-positive larvae were selected along with one EGFP-negative larva as a negative control. Total genomic DNA was extracted from individual larvae as described above. The average total yield of DNA from a single PBW larva was 17 μg.

From the foregoing, it will be appreciated that, although specific embodiments of the invention have been described herein for the purpose of illustration, various modifications may be made without deviating from the spirit and scope of the invention.

What is claimed is:

1. An expression cassette comprising a promoter sequence having at least 90% identity with the sequence set forth in SEQ ID NO:1 operably linked to a heterologous nucleic acid sequence encoding a protein of interest,
   wherein the promoter drives expression of the protein of interest in an insect.

2. The expression cassette of claim 1, further comprising a transcriptional enhancer.

3. The expression cassette of claim 1, further comprising a regulatory sequence that controls the tissue-specific expression of said protein of interest.

4. The expression cassette of claim 1, wherein said protein is a fluorescent marker.

5. The expression cassette of claim 4, wherein said fluorescent marker is the enhanced green fluorescent protein.

6. The expression cassette of claim 4, wherein said fluorescent marker is DSred.

7. The expression cassette of claim 1, wherein said nucleic acid sequence encodes a therapeutic protein.

8. The expression cassette of claim 1, wherein said nucleic acid sequence is linked to said promoter sequence in an antisense orientation.

9. An expression vector comprising the expression cassette according to claim 1.

10. The expression vector of claim 9, wherein said expression vector is a transposable element.

11. The expression vector of claim 10, wherein said transposable element is piggyBac.

12. The expression vector of claim 11, wherein said piggyBac element lacks about 1 kb from the Open Reading Frame encoding the transposase.

13. A host cell transfected with the recombinant expression cassette of claim 1.

14. The expression cassette of claim 1, wherein the insect is a Lepidopteran.

* * * * *

SEQUENCE LISTING

<160> NUMBER OF SEQ ID NOS: 14

<210> SEQ ID NO 1
<211> LENGTH: 172
<212> TYPE: DNA
<213> ORGANISM: Bombyx mori
<220> FEATURE:
<223> OTHER INFORMATION: modified actin 3 promoter

<400> SEQUENCE: 1
cgaatgcgca ctgttcgagc acaccttagt aaatgagaac cgactcgtga ggataaacta      60
tataaaagag ccgttatcac aatttacaca gtatcggctc cagtttgttt ttccaccaat     120
cgcgggctga ctcagttttt gtcaccatat atggtaacgc gcacgctatc ag            172

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:BMUP primer

<400> SEQUENCE: 2
ccgaattctg atagcgtgcg cgttacc                                          27

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:BMDN primer

<400> SEQUENCE: 3
ccggatccga atgcgcactg ttcgag                                           26

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:EGUP primer

<400> SEQUENCE: 4
gggctgcagg aattctggag tcgac                                            25

<210> SEQ ID NO 5
<211> LENGTH: 28
<212> TYPE: DNA
<213> ORGANISM: Artificial Sequence

```
<220> FEATURE:
<223> OTHER INFORMATION: Description of Artificial Sequence:EGDN primer

<400> SEQUENCE: 5
gggaagatct tgatgagttt ggacaaac                                          28

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:2781F primer

<400> SEQUENCE: 6
gcgatgacga gcttgttggt g                                                 21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:2519R primer

<400> SEQUENCE: 7
tccaagcggc gactgagatg                                                   20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:4788F primer

<400> SEQUENCE: 8
cctcgatata cagaccgata aaac                                              24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:4447R primer

<400> SEQUENCE: 9
tgcatttgcc tttcgcctta t                                                 21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:5SEQ primer

<400> SEQUENCE: 10
cgcgctattt agaaagagag ag                                                22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:3SEQ primer

<400> SEQUENCE: 11
cgataaaaca catgcgtcaa tt                                                22
```

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:primer #1

<400> SEQUENCE: 12
gtcacaacaa catcaagctg                                                    20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:primer #2

<400> SEQUENCE: 13
ctggctgcat aagcagttg                                                     19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:primer #3

<400> SEQUENCE: 14
cttcgattat ttgtagctct g                                                  21
```